United States Patent [19]

Santiesteban et al.

[11] Patent Number: 5,741,906
[45] Date of Patent: Apr. 21, 1998

[54] PRODUCTION OF TRIETHYLENEDIAMINE USING SURFACE ACIDITY DEACTIVATED ZEOLITE CATALYSTS

[75] Inventors: Jose Guadalupe Santiesteban; Hong-Xin Li, both of Allentown; John Nelson Armor, Orefield, all of Pa.

[73] Assignee: Air Products and Chemicals, Inc., Allentown, Pa.

[21] Appl. No.: 751,143

[22] Filed: Nov. 15, 1996

[51] Int. Cl.$^6$ .................................................. C07D 487/08
[52] U.S. Cl. .................................................. 544/352; 544/351
[58] Field of Search .................................................. 544/351, 352

[56] References Cited

U.S. PATENT DOCUMENTS

| | | | |
|---|---|---|---|
| 3,442,795 | 5/1969 | Kerr et al. | 208/120 |
| 3,443,795 | 5/1969 | Gresens et al. | 259/11 |
| 3,956,329 | 5/1976 | Murakami et al. | 260/268 SY |
| 4,388,177 | 6/1983 | Bowes et al. | 208/111 |
| 4,701,431 | 10/1987 | Pine | 502/73 |
| 4,804,758 | 2/1989 | Hoelderich et al. | 544/352 |
| 4,814,303 | 3/1989 | Chowdhry | 501/119 |
| 4,918,233 | 4/1990 | Deehu | 564/479 |
| 4,966,969 | 10/1990 | Sato et al. | 544/352 |
| 5,041,548 | 8/1991 | Sato et al. | 544/352 |
| 5,242,676 | 9/1993 | Apelian | 423/714 |
| 5,304,695 | 4/1994 | Haag et al. | 585/666 |
| 5,567,666 | 10/1996 | Beck et al. | 502/71 |

FOREIGN PATENT DOCUMENTS

| | | |
|---|---|---|
| 0158319 | 10/1985 | European Pat. Off. . |
| 290862 | 11/1988 | European Pat. Off. ............. 544/352 |
| 03122734 | 4/1989 | European Pat. Off. . |
| 0313753 | 5/1989 | European Pat. Off. . |
| 0423526 | 4/1991 | European Pat. Off. . |

OTHER PUBLICATIONS

Chen, N. Y., Degnan, Jr., Thomas F., and Smith, C. Morris "Molecular Transport and Reaction in Zeolites" VHC Publishers, Inc. 1994, pp. 15 and 17.
Translation of EP382 055 (1990).

*Primary Examiner*—Mark L. Berch
*Attorney, Agent, or Firm*—Michael Leach; William F. Marsh

[57] ABSTRACT

A process for preparing triethylenediamine by passing an ethanolamine, ethyleneamine, piperazine or morpholine over a pentasil-type zeolite at elevated temperature characterized by employing a ZSM-5 zeolite in the hydrogen or ammonium form which has been pretreated with an aqueous solution of a chelating agent capable of forming a chelate-aluminum complex.

18 Claims, No Drawings

PRODUCTION OF TRIETHYLENEDIAMINE USING SURFACE ACIDITY DEACTIVATED ZEOLITE CATALYSTS

BACKGROUND OF THE INVENTION

The present invention relates to the preparation of triethylenediamine (TEDA) by contacting nitrogen-containing compounds with zeolites at elevated temperature. The synthesis of TEDA from a variety of amine compounds using metallosilicates is well known in the art.

U.S. Pat. No. 3,956,329 discloses a process for preparing TEDA from a number of amine compounds using untreated zeolite catalysts with a $SiO_2/Al_2O_3$ (silica to alumina) ratio between 2 and 12.

U.S. Pat. No. 4,804,758 discloses the preparation of TEDA from certain heterocyclic amines in the presence of borosilicate and/or iron silicate zeolites as catalysts.

U.S. Pat. Nos. 4,966,969 and 5,041,548 disclose the preparation of TEDA from amine compounds using a catalyst comprising a crystalline metallosilicate having a silica/metal oxide molar ratio of 12/1 or more, in particular, a metallosilicate crystallized in the presence of an organic crystallizing agent.

EP 158 319 discloses a method of preparing TEDA by contacting acyclic or heterocyclic amines with untreated high-silica zeolite having a silica to alumina ratio of at least 20 to 1.

EP 382 055 discloses a process for synthesizing TEDA from ethylenediamine and 0 to 200 mole % piperazine on aluminum, boron, gallium and/or iron silicate zeolites.

EP 423 526 discloses the preparation of TEDA and piperazine from ethylenediamine-water mixtures which is catalyzed by zeolites of the pentasil type with weakened acidity, i.e., which contain alkali metal ions or in which the aluminum of the zeolite skeleton has been isomorphously replaced by iron.

EP 312 734 discloses that piperazine can be converted directly to TEDA in the presence of untreated zeolites having a pentasil, especially a ZSM-5, structure.

EP 313 753 discloses the preparation of mixtures of TEDA and piperazine from polyethylene polyamines and/or ethanolamines using an untreated pentasil zeolite.

The following references disclose treatment of zeolites with chelating agents:

U.S. Pat. No. 3,442,795 discloses a process for preparing highly siliceous zeolite-type materials from a crystalline aluminosilicate by hydrolysis followed by a chelation step.

U.S. Pat. Nos. 4,388,177 and 5,304,695 disclose oxalic treatments of zeolites to improve their catalytic properties for hydrocarbon conversion reactions.

BRIEF SUMMARY OF THE INVENTION

The present invention is directed to a process for preparing TEDA by contacting an amine-containing compound with a pentasil-type zeolite in the hydrogen (H+) and/or ammonium ($NH_4$+) form at elevated temperatures. The zeolite catalyst used in the process is one whose surface has been at least partially dealuminated prior to its conversion to the H+ or $NH_4$+ form. Dealumination can be performed by treating the zeolite with an aluminum chelating agent.

Such dealumination treatment at least partially and permanently deactivates the external sites of the zeolite catalyst for acid catalyzed reactions and surprisingly improves the selectivity toward TEDA production. Some of the amine compounds typically used in making TEDA, such as ethylenediamine (EDA), are very reactive on the external sites of zeolite catalysts giving undesired products.

BRIEF DESCRIPTION OF THE SEVERAL VIEWS OF THE DRAWINGS

Not Applicable

DETAILED DESCRIPTION OF THE INVENTION

As the starting material to be used in the process for preparing TEDA, any amine compounds having, in the molecule, a moiety represented by the following general formula can be used:

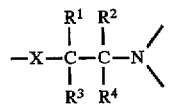

where $R^1$, $R^2$, $R^3$ and $R^4$ are independently a hydrogen atom or an alkyl group having 1 to 4 carbon atoms and X is oxygen or nitrogen. Typical examples of suitable amine compounds are ethanolamines, including monoethanolamine, diethanolamine and triethanolamine; isopropanolamines, including monoisopropanolamine and diisopropanolamine; ethyleneamines, including ethylenediamine, diethylenetriamine and triethylenetetramine; piperazine and its derivatives N-hydroxyethylpiperazine, bis-(hydroxyethyl)piperazine and N-aminoethylpiperazine; morpholine and obviously mixtures of the foregoing.

The crystalline metallosilicate (zeolite), which is used as the catalyst in the process, has a crystal skeleton mainly comprised of silicon dioxide (silica; $SiO_2$) and a metal oxide such as aluminum oxide (alumina; $Al_2O_3$), iron oxide or boron oxide. Alumina is the preferred metal oxide. The silica/metal oxide molar ratio is 12:1 or more, preferably 20:1 to 1000:1, and more preferably 50:1 to 500:1. If the silica/metal oxide molar ratio is less than 12:1, the yield of TEDA is undesirably low.

There are no special limitations to the crystalline aluminosilicate that is used as long as it satisfies the above silica/alumina molar ratio. Crystalline aluminosilicates having a main pore made of a ten-member ring of oxygen, especially those belonging to members of the pentasil-type structure, are preferred with ZSM-5 zeolite being most preferred.

The preparation of suitable pentasil zeolite catalysts is well known to those skilled in the art as illustrated by the previously cited patents and literature references. In addition, suitable pentasil zeolites are commercially available from many sources such as Degussa AG and CU Chemie Uetikon AG.

Crystalline aluminosilicates of the pentasil family as obtained by the hydrothermal synthesis using an organic crystallizing agent are particularly preferred. Among the pentasil types, the zeolite structures ZSM-5, ZSM-11, ZSM-8, and ZSM-5/ZSM-11-intermediates are preferred, especially ZSM-5.

The zeolite catalysts are used in their hydrogen form (H+) and/or their ammonium form ($NH_4$+) after having undergone the dealumination treatment.

For example, a pentasil-type crystalline aluminosilicate can be prepared by the hydrothermal synthesis using a mixture composed mainly of a silica source, e.g., colloidal silica, silica gel, or silicic acid salts such as water glass, and an aluminum oxide source, e.g., the sulfuric acid salts, nitric acid salts or oxy acid salts of alumina, such as aluminum sulfate and sodium aluminate, in the absence or preferably in the presence of an organic crystallizing agent, e.g., amines such as tetraalkylammonium halide having 2 to 5 carbon atoms.

There is also known a method in which the hydrothermal synthesis is performed in the presence of alkali metal compounds such as the hydroxides and halides of alkali metal such as sodium and the like.

The crystalline aluminosilicate obtained by these methods is generally not of the H+ or $NH_4+$ form, but of the form that H+ and $NH_4+$ are replaced by quaternary ammonium ion and/or alkali metal ion such as Na+ and the like. Therefore, the crystalline aluminosilicate must be changed into the H+ or $NH_4+$ form, and this exchange can be easily achieved by known methods.

With regard to the dealumination treatment, the prepared aluminosilicate is contacted, for example, with an aqueous 0.1 to 5 molar solution of an aluminum-chelating agent, i.e., a chelating agent capable of forming a chelate-Al complex, such as polycarboxylic acids, ethylenediaminetetraacetic acid (EDTA), nitrilotriacetic acid, and acetylacetone (AcAc), at 0° to 100° C. for sufficient time to effect partial or total surface dealumination, e.g., 0.01 to 100 hours, preferably 0.5 to 3 molar chelating agent solution at 40° to 90° C. for 0.5 to 5 hours. It is desirable to perform such contact using 5 to 100 mL aqueous solution/g zeolite.

Suitable dicarboxylic acids for use as aluminum-chelating agents include oxalic, malonic, succinic, glutaric, adipic, tartaric, maleic and phthalic acids and mixture of these acids. Tricarboxylic acids such as citric acid and higher polycarboxylic acids can also be used.

The treatment with chelating agent is believed to bind selectively with aluminum from the crystal surface of the zeolite, rendering the aluminum inactive as an acid site and capable of removal from the zeolite by filtration and optionally with subsequent washing with a suitable solvent, e.g., water or organic solvents. The treatment can be combined with other conventional techniques, such as steaming and chemical treatment with inorganic compounds.

For changing the alkali metal ion of the chelate-treated zeolite into H+ or $NH_4+$, there is often employed a method in which the alkali metal salt-type crystalline aluminosilicate is treated with an aqueous solution of ammonium salts, such as ammonium nitrate and ammonium sulfate, to form an ammonium salt-type crystalline aluminosilicate. The ammonium salt-type crystalline aluminosilicate may then be calcined in the air at a temperature of 300° to 600° C., preferably 400° to 500° C. to obtain the H+ form crystalline zeolite.

While the zeolite as used in the present invention is preferably of the H+ and/or $NH_4+$ form, the H+ and/or $NH_4+$ may be partially replaced by other cations, such as alkali, alkaline earth, rare earth, transition metals, oxides etc., as long as the object of the present invention can be obtained.

The catalyst of the present invention can be used in any desired form, such as powder, particles, strips, spheres and pellets. The catalyst can be self-bound or molded with a binder such as silica, titania and/or zirconia. If alumina, natural clays and/or mixtures of these materials are to be mixed with the zeolite, the zeolite should be first treated with the dealuminating agent. Naturally occurring clays which can be composited with the zeolite catalyst include the montmorillonite and kaolin family. These clays can be used in the raw state as originally mined or initially subjected to calcination, acid treatment or chemical modification.

Of all the matrix materials mentioned above, materials of low acidity such as silica or zirconia are preferred in that they prevent unwanted side reactions engendered by more active materials such as alumina. The performance of alumina can, however, be improved by altering its acid properties via chemical modification.

The relative proportions of zeolite and matrix material can vary widely with the zeolite content ranging from 10 to 98 wt %, and more usually in the range of 50 to 90 wt %, of the composite.

In accordance with the process of the present invention, the desired TEDA can be efficiently obtained by reacting amine compounds having in the molecule a group represented by the general formula:

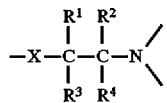

or preferably the general formula:

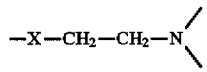

where $R^1$, $R^2$, $R^3$ and $R^4$ are independently a hydrogen atom or an alkyl group having 1 to 4 carbon atoms and X is nitrogen or oxygen as the starting material using the described zeolite catalyst under pressures ranging from 0.001 to 200 atm (0.1 to 20,000 kPa), preferably 0.01 to 10 atm (1 to 1000 kPa).

The reaction of the amine compound proceeds on contacting it with the described zeolite catalyst under the above-specified pressure. Reaction conditions, such as reaction temperature, reaction time and starting materials/catalyst ratio, cannot be determined unconditionally because they vary with the type of amine compound, the type of zeolite catalyst, reaction pressure and the like. Usually the reaction temperature is chosen within the range 100° to 450° C., preferably 300° to 400° C.

The reaction can be performed batch-wise, semi-continuously or continuously. In the case of the continuous reaction, WHSV (weight hourly space velocity) is not critical, but usually ranges from 0.01 to 10 $hr^{-1}$. The preferred WHSV is determined depending on the temperature. For example, at 300° C., WHSV is 0.02 to 2 $hr^{-1}$, and at 350° C., it is 0.1 to 5 $hr^{-1}$.

In the reaction of the amine compound as a starting material, it may be diluted with an inert gas such as hydrogen, nitrogen, steam or hydrocarbons, or with an inert solvent such as water and inert hydrocarbons. By using these diluents, the reaction can be controlled appropriately.

EXAMPLE 1

Preparation of HZSM-5

A 40 g NaZSM-5 sample (obtained from Degussa AG Modul 180) was exchanged with 800 mL of 1.0M aqueous $NH_4NO_3$ solution. The solid was filtered, washed with deionized water, and dried at 110° C. to yield $NH_4$-ZSM-5. HZSM-5 was obtained by calcination of the $NH_4$-ZSM-5 at 500° C.

EXAMPLE 2

Preparation of oxalic acid-treated HZSM-5

An oxalic acid treated ZSM-5 sample was prepared by treating 15 g of ZSM-5 catalyst of Example 1 with 500 mL of an aqueous 2M oxalic acid solution at about 80° C. for 5 hours, then cooled to ambient temperature. The solid was filtered and washed with deionized water to remove excess oxalic acid, then dried at 150° C. for 2 hours. The resulting catalyst was tested for TEDA synthesis as described in Examples 4 and 6.

EXAMPLES 3 AND 4
TEDA Synthesis from MELA/PIP

The reactions were carried out in a plug-flow reactor at atmospheric pressure and 350° C. An aqueous monoethanolamine/piperazine (MELA/PIP) solution consisting of 3.8 wt % MELA/11 wt % PIP/85.2 wt % H2O was fed to the reactor with an ISCO pump. The flow rate, expressed as WHSV=g organic feed per g zeolite per hour, was 0.2 hr$^{-1}$. Ammonia was co-fed to the reactor in a NH3/MELA molar ratio of 3/1. The results obtained on the untreated and oxalic acid treated ZSM-5 catalysts for TEDA synthesis from the MELA/PIP feedstock mixture are shown in Examples 3 and 4, respectively, of Table 1.

EXAMPLES 5 AND 6
TEDA Synthesis from MELA/DELA

The reactions were carried out in a plug-flow reactor at atmospheric pressure and 350° C. An aqueous MELA DELA solution consisting of 11 wt % MELA 19 wt % PIP/70 wt % H2O was fed to the reactor with an ISCO pump. The flow rate, expressed as WHSV=g organic feed per g zeolite per hour, was 0.52 h–$^{1}$. Ammonia was co-fed to the reactor in a NH$_3$/MELA molar ratio of 2/1. The results obtained on the untreated and oxalic acid treated ZSM-5 catalysts for TEDA synthesis from the MELA/DELA feedstock mixture are shown in Examples 5 and 6, respectively, of Table 1.

TABLE 1

| Example | Catalyst From Ex. | Oxalic Acid Treatment | Conversion (%) MELA | Conversion (%) PIP | Conversion (%) MELA | Conversion (%) DELA | TEDA Molar Sel. (%) |
|---|---|---|---|---|---|---|---|
| 3 | 1 | No | 100 | 72 | — | — | 10 |
| 4 | 2 | Yes | 72 | 69 | — | — | 30 |
| 5 | 1 | No | — | — | 43 | 53 | 19 |
| 6 | 2 | Yes | — | — | 36 | 49 | 25 |

The data in Table 1 clearly show the beneficial effect of TEDA selectivity upon treating ZSM-5 zeolite with oxalic acid.

INDUSTRIAL APPLICATION

The present invention provides an improvement in the production of TEDA from amine compounds using a zeolite catalyst.

We claim:

1. In a process for preparing triethylenediamine by passing an amine compound which is monoethanolamine, diethanolamine, triethanolamine, ethylenediamine, diethylenetriamine, triethylenetetramine, piperazine, N-hydroxyethylpiperazine, bis(hydroxyethyl)-piperazine, N-aminoethylpiperazine, morpholine or a mixture thereof over a pentasil-type zeolite at elevated temperature, the improvement which comprises employing a pentasil-type zeolite in the hydrogen or ammonium form which has been treated with a dealuminating agent.

2. The process of claim 1 in which the dealuminating agent is a chelating agent capable of forming a chelate-aluminum complex.

3. The process of claim 2 in which the chelating agent is a polycarboxylic acid, ethylenediaminetetraacetic acid, nitrilotriacetic acid, or acetylacetone.

4. The process of claim 2 in which the chelating agent is a dicarboxylic acid.

5. The process of claim 2 in which the chelating agent is oxalic acid, malonic acid, succinic acid, glutaric acid, adipic acid, tartaric acid, maleic acid, phthalic acid or a mixture thereof.

6. The process of claim 5 in which the dealuminated zeolite has a silica/metal oxide molar ratio of 20:1 to 1000:1.

7. The process of claim 6 in which the zeolite is a ZSM-5, ZSM-8 or ZSM-11 zeolite.

8. In a process for preparing triethylenediamine by passing an amine compound which is monoethanolamine, diethanolamine, triethanolamine, ethylenediamine, diethylenetriamine, triethylenetetramine, piperazine, N-hydroxyethylpiperazine, bis(hydroxyethyl)-piperazine, N-aminoethylpiperazine, morpholine or a mixture thereof, over a pentasil-type zeolite at elevated temperature, the improvement which comprises employing a ZSM-5 zeolite in the hydrogen or ammonium form which has been pretreated with a chelating agent which is capable of forming a chelate-aluminum complex.

9. In a process for preparing triethylenediamine by passing monoethanolamine, diethanolamine, triethanolamine, ethylenediamine, diethylenetriamine, triethylenetetramine, piperazine, N-hydroxyethylpiperazine, bis(hydroxyethyl) piperazine, N-aminoethylpiperazine, morpholine or a mixture thereof over a pentasil-type zeolite at elevated temperature, the improvement which comprises employing a ZSM-5 zeolite having a silica/alumina molar ratio of 20:1 to 1000:1 in the hydrogen or ammonium form which has been pretreated with a 0.1 to 5 molar aqueous solution of a chelating agent capable of forming a chelate-aluminum complex which is a dicarboxylic acid, ethylenediaminetetraacetic acid, nitrilotriacetic acid, or acetylacetone.

10. The process of claim 9 in which the dealuminated zeolite has a silica/alumina molar ratio of 50:1 to 500:1.

11. The process of claim 8 in which the dealuminated zeolite has a silica/alumina molar ratio of 20:1 to 1000:1.

12. The process of claim 11 in which the amine compound is monoethanolamine, diethanolamine, piperazine or a mixture thereof.

13. The process of claim 12 in which the chelating agent is a dicarboxylic acid, ethylenediaminetetraacetic acid, nitrilotriacetic acid, or acetylacetone.

14. The process of claim 13 in which the chelating agent is a dicarboxylic acid.

15. The process of claim 10 in which the chelating agent is a dicarboxylic acid.

16. The process of claim 15 in which the amine compound is selected from the group consisting of (1) monoethanolamine and piperazine and (2) monoethanolamine and diethanolamine.

17. The process of claim 6 in which the dicarboxylic acid is oxalic acid.

18. The process of claim 17 in which the zeolite is treated with 5 to 100 mL of 0.5 to 3 molar aqueous oxalic acid solution per gram zeolite.

* * * * *